(12) United States Patent
Arkharov et al.

(10) Patent No.: US 6,212,904 B1
(45) Date of Patent: Apr. 10, 2001

(54) LIQUID OXYGEN PRODUCTION

(75) Inventors: Ivan A. Arkharov; Alexey M. Arkharov, both of Moscow (RU); Leslie C. Kun, Williamsville; Tommy M. Tetreault, Grand Island, both of NY (US)

(73) Assignee: In-X Corporation, Lakewood, CO (US)

( * ) Notice: Subject to any disclaimer, the term of this patent is extended or adjusted under 35 U.S.C. 154(b) by 0 days.

(21) Appl. No.: 09/431,447

(22) Filed: Nov. 1, 1999

(51) Int. Cl.[7] .................................................. F25J 1/00
(52) U.S. Cl. .............................. 62/615; 62/47.1; 62/51.2; 62/616; 62/911
(58) Field of Search .......................... 62/615, 616, 47.1, 62/51.2, 911

(56) References Cited

U.S. PATENT DOCUMENTS

| | | | |
|---|---|---|---|
| 4,279,127 | * | 7/1981 | Longsworth ........................... 62/47.1 |
| 4,666,480 | * | 5/1987 | Mann ..................................... 62/616 |
| 4,967,564 | * | 11/1990 | Strasser ................................. 62/47.1 |
| 5,077,979 | * | 1/1992 | Skertic et al. ........................ 62/51.2 |
| 5,327,729 | * | 7/1994 | Yanai et al. ............................ 62/47.1 |
| 5,893,275 | | 4/1999 | Henry ..................................... 62/615 |

FOREIGN PATENT DOCUMENTS

WO 98/58219   12/1998   (WO).

\* cited by examiner

*Primary Examiner*—Ronald Capossela
(74) *Attorney, Agent, or Firm*—Sheridan Ross P.C.

(57) ABSTRACT

An apparatus for liquefying and storing a gas is provided. The apparatus is adapted to liquify relatively small quantities of gas, and to do so in a residence or place of business. The apparatus generally includes a cryocooler, a heat transfer assembly, and an insulated subsystem. Liquid condensate produced by the apparatus is stored in an insulated dewar. The method of the present invention includes the liquification of air or an enriched gas on a small scale in a residence or place of business. The method and apparatus of the invention are particularly well suited for providing liquified oxygen for use by a patient on oxygen therapy in the patient's residence.

34 Claims, 7 Drawing Sheets

LIQUID OXYGEN PRODUCTION

FIELD OF THE INVENTION

The present application relates to the production and storage of liquified gases at the site where at least some of the liquified gas is to be use. In particular, the present invention relates to the production and storage of liquid oxygen in an oxygen patient's residence.

BACKGROUND OF THE INVENTION

The liquification of low boiling point gases, such as air and the components of air, such as oxygen, nitrogen and argon, has been practiced for over 100 years, and the liquification of such gases on an industrial scale has been practiced since the beginning of the 20th century. Typically, commercial liquefiers are designed to produce hundreds of tons of liquid cryogens per day. Such industrial liquefiers are reliable, and are capable of producing liquified gas with relatively high energy efficiency. For consumers of liquified gas requiring relatively small quantities, small insulated containers, known as dewars, are filled with liquified gas produced by commercial facilities and transported to the consumer. Consumers of small quantities of liquified gas include hospitals, which require oxygen for delivery to patients and nitrogen for use as a refrigerant. Also, people suffering from chronic respiratory insufficiency that have been prescribed home oxygen by their physicians may have liquified oxygen delivered to their residences.

However, the cost of distributing small quantities of liquified gas is relatively high. In addition, frequent deliveries of liquified gases must be made because of losses due to the eventual warming and boil-off of liquified gas stored in containers. Therefore, there is a need for a liquefier capable of efficiently producing liquified gas at the point of use. For instance, there is a need for a liquefier capable of producing in the range of 0.4 to 5 kilograms per day of liquid oxygen for use in an oxygen patient's residence, or similar amounts of liquid nitrogen for use in physicians' offices or in labs, where it may be used for freezing skin lesions or refrigerating biological samples.

Initially, attempts to provide such a liquefier involved efforts to miniaturize large scale liquefying plants. However, due to the complexity of such systems, which are typically based on the Claude cycle or its variants, these attempts failed. Also, the extremely small mechanical components resulting from the miniaturization of such liquefiers were expensive to produce and unreliable in operation.

In recent years, cryocoolers have been intensively developed. Initially, cryocoolers were developed for the military for use in such applications as cooling infrared sensors, semiconductor chips, microwave electronics, high temperature superconductivity applications, fiber optic amplifiers, etc. The cryocoolers developed for these applications operated in a temperature range of from about 20K to 150K, and their cooling capacity ranged from less than a watt to over 100 watts. For such military applications, the cryocoolers were required to have particular features. For example, in some applications, a fast cool down is important. In other applications, low noise and vibration are desirable. Also, in certain applications, for instance those used in connection with electronic devices, close temperature control of the cooling head is important. Furthermore, certain applications were concerned with preventing frost formation on the insulating envelope and humidity ingress to the cooling components. In addition, the cryocoolers developed for the above-described military applications provided their heat input at or near the lowest temperature point of the cryocooler. For instance, the component to be cooled was typically attached to the cold point (the "cold finger") of the cryocooler, transferring heat directly to that component, with minimal conduction losses. However, for use in small scale gas liquefiers, features such as precise temperature control and quick cool down are not necessary, and serve only to increase the cost of the device. Also, point cooling is inefficient for use in liquefying gases.

With respect to the need for relatively small but steady quantities of oxygen by patients on oxygen therapy, there have been several ways in which the needs of such patients have been met. The most common method for oxygen therapy patients to receive oxygen is through regular deliveries of oxygen produced at a commercial plant. The oxygen may be delivered as either a pressurized gas or as a liquid. When delivered as a pressurized gas, the oxygen presents a hazard because of the high pressure under which it is stored and because oxygen is highly reactive. Oxygen delivered as a liquid is subject to losses resulting from boil-off, which occurs due to the inevitable warming of the liquified gas over time. Because such losses occur even when specially insulated containers, or dewars, are used, deliveries of fresh liquid oxygen must be made on a weekly basis.

It is also known to provide devices which extract or concentrate oxygen found in the ambient air. These devices obviate the need to store a potentially hazardous material. However, these devices are typically not portable, and therefore a person on continuous oxygen therapy must continue to rely on oxygen that has been "bottled" commercially in order to leave their residences. Such reliance has been necessary because, although oxygen concentrators having a production capacity greater than the needs of oxygen patients are known, there has not been an available apparatus and method for producing and storing liquid oxygen in a residence.

For the above-stated reasons, it would be advantageous to provide a method and apparatus for producing and storing relatively small quantities of liquified gas at the location where the liquified gas is to be used. In particular, it would be advantageous to provide a method and apparatus for liquefying oxygen produced in an oxygen therapy patient's residence. In addition, it would be advantageous to provide such a method and device that is economical to operate and reliable.

SUMMARY OF THE INVENTION

In accordance with the present invention, a system for liquefying gas on a relatively small scale is provided. The disclosed system generally includes a cryocooler, a heat exchanger assembly, and an insulated subsystem. The system operates by cooling a feed gas to a point below the boiling temperature of that feed gas, and storing the resulting liquid condensate.

The cryocooler may operate according to any one of a number of well known thermodynamic cycles. The cold finger of the cryocooler is associated with the heat exchanger assembly, which receives the incoming feed gas. In a preferred embodiment, the heat exchanger assembly includes a sensible heat exchanger featuring cooling fins or other means to increase the surface area of the heat exchanger assembly cooled by the cold finger of the cryocooler. This maximizes contact with the incoming feed gas, increasing the cooling efficiency of the device. The insulated subsystem generally extends about the periphery of the heat exchanger assembly, insulating that assembly from the ambient temperature. In this way, the cold components of the device are insulated from losses to the atmosphere. The insulated subsystem further includes an insulated storage space, such as a storage dewar, for collection and storage of the liquid condensate produced in the heat exchanger assembly.

The disclosed system may, in a preferred embodiment, be adapted for providing liquified oxygen for use in an oxygen patient's residence. Accordingly, the disclosed system is particularly well adapted for producing from approximately 0.4 to 5 kilograms per day of liquid oxygen. Additionally, the described system may be provided with means for transferring liquified gas produced by the system to other devices, such as portable storage dewars. Accordingly, when used to produce liquified oxygen, the condensate so produced may be transferred to portable storage dewars, to allow the oxygen therapy patient to take a supply of oxygen with them when leaving the residence.

The disclosed method and apparatus provides an economical means for producing liquified gases on a relatively small scale. The system does so by providing an apparatus that is relatively simple mechanically, economical to assemble, and easy to use. Use of the disclosed system also avoids the need to have liquid oxygen or other liquified gases delivered to the point of use, which has been proven to be inefficient in transportation costs and in losses due to boil-off caused by the inevitable warming of the liquified gas between production and ultimate use. Accordingly, by producing the liquified gas at the point of use, the need to transport liquified gas is eliminated, and the time that the liquified gas must be stored before it is used is reduced.

Based on the foregoing summary, a number of salient features of the present invention are readily discerned. A method and apparatus for liquefying small quantities of gas is provided. The invention allows liquified gas to be produced in a residential or business setting, providing for the production of liquified gas on demand, and obviating the need for users having a requirement for a small but steady supply of liquified gas to receive regular and frequent deliveries of such gas from off-site producers.

Additional advantages of the present invention will become readily apparent from the following discussion, particularly when taken together with the accompanying drawings.

DETAILED DESCRIPTION

In accordance with the present invention, a method and apparatus for producing and storing liquid oxygen in an oxygen patient's residence is provided.

Figure 1:
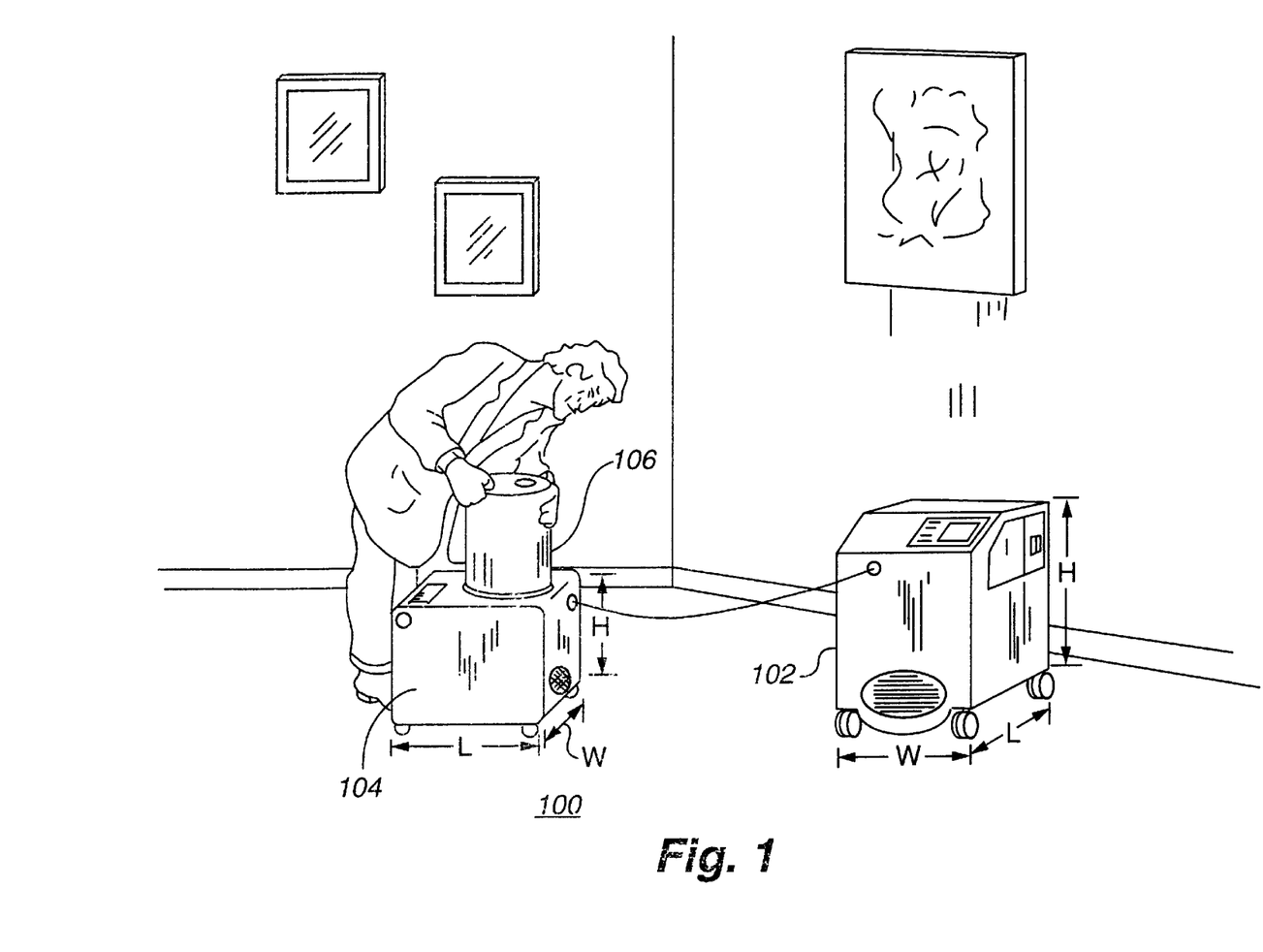
FIG. 1 depicts the use of a bimodular version of the liquified gas production system by a home oxygen patient.

With reference to FIG. 1, an embodiment of a system 100 for producing and storing liquid oxygen in an oxygen patient's residence is depicted. The system 100 includes an oxygen concentration subsystem 102 for producing an oxygen enriched gas from ambient air, and a cryogenic subsystem 104 for liquefying and storing oxygen provided by the oxygen concentrator 102. The cryogenic subsystem 104 may include a portable storage dewar 106, which allows the oxygen patient to carry liquified oxygen produced by the system 100 when the patient is away from home. Although the system 100 is depicted in FIG. 1 as a bimodular system, it may also be provided in a single cabinet.

Figure 2:
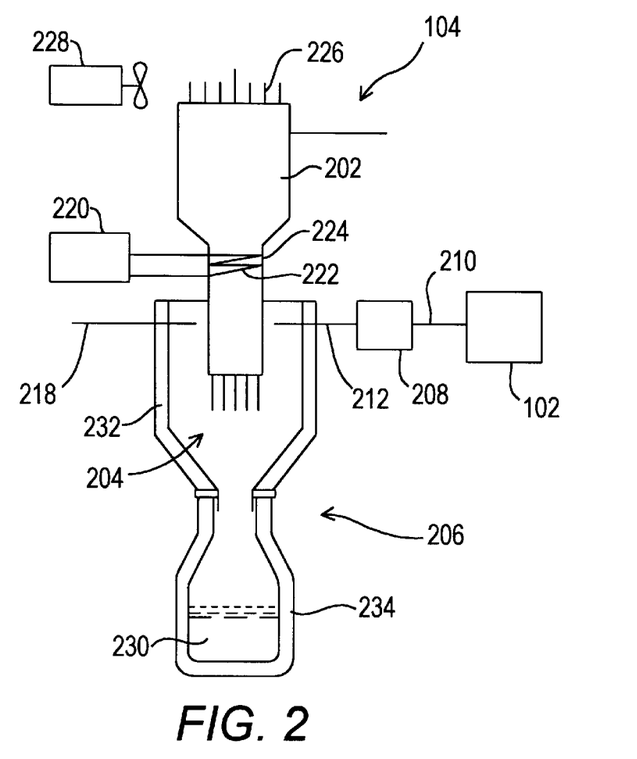
FIG. 2 is a schematic depiction of the cryogenic subsystem of the present invention.

Referring now to FIG. 2, the major components of the cryogenic subsystem 104 and its interconnection to the oxygen concentration subsystem 102 are depicted schematically. These components generally include a cryocooler 202, a heat exchanger assembly/condenser 204, and an insulated subsystem 206. In a preferred embodiment, the configuration of the cryogenic subsystem 104 is as illustrated in FIG. 2, with the cryocooler 202 on top, and the insulated subsystem 206 below and surrounding the heat exchanger assembly/condenser 204.

The cryogenic subsystem 104 is supplied with an oxygen enriched feed gas by the concentrator subsystem 102. In the configuration illustrated in FIG. 2, the oxygen enriched feed gas is supplied to a final filter 208 by a conduit 210. From the final filter 208, the oxygen enriched feed gas is supplied to the heat exchanger/condenser assembly 204 of the cryogenic subsystem 104 by a feed gas tube 212. The oxygen enriched gas is cooled and liquified in the heat exchanger/condenser assembly 204. Waste gases and boil-off exit the cryogenic subsystem 104 through waste conduit 218.

Also illustrated in FIG. 2 are means for improving the cooling capacity of the cryocooler 202. These include a vapor compression refrigeration system 220 having an evaporator 222 wrapped about the heat rejection area 224 of the cryocooler 202. Additionally, the cryocooler 202 may be provided with cooling fins 226 to assist in the removal of waste heat from the cryocooler 202. A fan 228 may be provided to direct a flow of air over the cooling fins 226, further increasing the rejection of heat, thereby increasing the efficiency and cooling capacity of the cryocooler 202.

The insulating subsystem 206 serves to insulate the heat exchanger assembly/condenser 204 from the outside environment and to provide an insulated storage space for storing the condensate 230 produced from the cooling of the feed gas in the heat exchanger assembly/condenser 204. As illustrated in FIG. 2, the insulating subsystem 206 may include an upper insulating element 232 as well as an insulated dewar 234. The insulating element 232 increases the efficiency and the cooling capacity of the device by insulating the cold components of the cryocooler 202 and the heat exchanger assembly/condenser 204 from the ambient air. The storage dewar 234 collects and stores the cold condensate 230 produced from the feed gas. The storage dewar may be any thermally insulated container. According to one embodiment, the storage dewar 234 is a 1.8 liter glass vacuum-insulated storage container.

Figure 3:
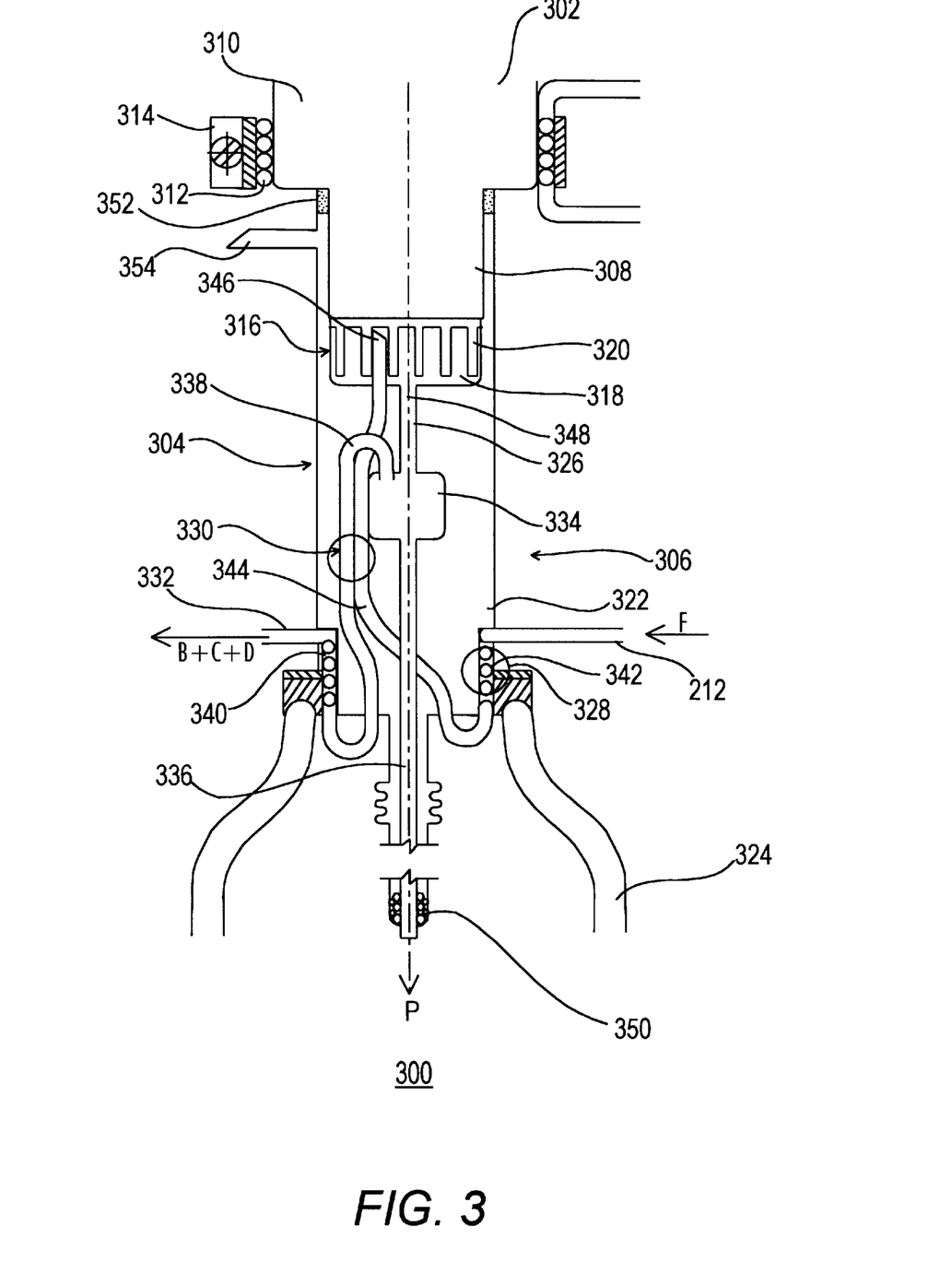
FIG. 3 is a partial depiction of the major components of a cryogenic subsystem according to an embodiment of the present invention.

Referring now to FIG. 3, a partial cross section of portions of the cryocooler subsystem 104 according to a first embodiment 300 is illustrated. As with the system described above, the major components of the cryocooler subsystem 300 are a cryocooler 302, a heat exchanger assembly 304 and an insulated subsystem 306. According to the embodiment of the cryocooler subsystem illustrated in FIG. 3, the components are generally arranged vertically, with the cryocooler 302 on top, the heat exchanger assembly 304 generally below the cryocooler 302, and the insulated subsystem 306 below and surrounding the heat exchanger assembly 304. This configuration generally assists in the production and collection of an oxygen-enriched condensate as described more fully below.

The cryocooler 302 generally includes a cold finger 308 and a heat rejection area 310. The heat rejection area 310 in the illustrated embodiment is surrounded by the evaporator 312 of a vapor compression refrigerator (not shown in FIG. 3), which is held against the heat rejection area 310 by a clamp 314. The vapor compression refrigerator is used to lower the temperature of the heat rejection area 310 of the cryocooler 302 to about −15° C. to −5° C., improving the refrigeration capacity of the cryocooler 302 by promoting the removal of heat from the heat rejection area 310. The flow of heat from the heat rejection area 310 to the evaporator 312 may be aided by the use of a heat conducting grease by reducing the impediment to heat flow due to contact resistance. The heat rejection from the heat rejection area 310 can be further improved by providing an annular space about the heat rejection area 310 in which to boil the refrigerant of the vapor compression refrigerator. The heat transfer to the refrigerant could be further improved by using a sintered porous surface or a scored surface for the heat rejection area 310, as are well-known in the art.

The heat exchanger assembly 304 generally includes a sensible heat exchanger/condenser 316 and a condenser volume 318. The sensible heat exchanger/condenser 316 is placed in direct contact with the cold finger 308 of the cryocooler 302. Alternatively, and in a preferred embodiment, the sensible heat exchanger/condenser 316 has cooling fins 320 that are integral to the cold finger 308, to increase the surface area and maximize the heat transfer between the sensible heat exchanger/condenser 316, and to ensure the most efficient transfer of heat from to the feed gas. Where the cold finger 308 and the cooling fins 320 are formed from separate components, they are preferably brazed or soldered to one another to minimize the contact resistance. The condenser volume 318 is, in the illustrated embodiment, formed from a surface of the insulated subsystem 306.

As shown in the illustrated embodiment, the insulated subsystem 306 may include an insulating member 322, which extends all the way down to adsorbent 350, and an insulated storage dewar 324. The insulating member 322 preferably surrounds the sensible heat exchanger 316 on those sides of the heat exchanger 316 that are not coincident with the cold finger 308, and extends about a periphery of the cold finger 308 to a point towards the heat rejection area 310 of the cryocooler 302 at a first end. Also at a first end, the insulating member 322 forms the condenser volume 318, and encloses a two-phase flow conduit 326. A first pre-cooling heat exchanger 328 may be positioned at a second end of said insulating member 322. The insulating member 322 may enclose portions of the feed line 212, a second pre-cooling heat exchanger 330, a phase separator 334, a liquid conduit 336 and non-condensible gas conduit 338.

When the subsystem 300 is in operation, a feed gas is supplied from a concentrator subsystem 102 (not illustrated in FIG. 3) or other gas source to the cryogenic subsystem 300. In the embodiment of the cryocooler subsystem 300 partially illustrated in FIG. 3, the feed gas is initially passed through a first pre-cooling heat exchanger 328. The first pre-cooling heat exchanger 328 generally includes a coil 340 formed by wrapping a continuation of the feed line 212 about a portion of the insulating member 322. The coil 340 and the feed gas passing through it are cooled by waste gas produced during the liquefaction process (described in greater detail below). The waste gas is passed over the coil 340 of the first pre-cooling heat exchanger 328 in an annular first pre-cooling chamber 342. The oxygen-enriched feed gas, having been cooled to about 0° C., then continues through transfer line 344 to a second pre-cooling heat exchanger 330, generally located within the insulating member 322. The second pre-cooling heat exchanger 330 is formed by brazing or soldering a portion of the transfer line 344 to a portion of the waste stream or non-condensible gas conduit 338. Alternatively, the second pre-cooling heat exchanger 330 may be formed from a single piece of heat conductive material, with inlets and outlets for the transfer line 344 and the non-condensible gas conduit 338 provided, to allow for efficient heat transfer between the streams. After passing through the second pre-cooling heat exchanger 330, the feed gas has a temperature of approximately −25° C.

The feed gas is delivered to the sensible heat exchanger 316 at the feed tube outlet 346. Within the condenser volume 318, the feed gas is cooled by contact with the cooling fins 320 of the sensible heat exchanger 316. Condensate formed from the cooling of the feed gas falls to the bottom of the condenser volume 318 and enters the condensate collector 348. The condensate, together with gases that have been cooled but not liquified, pass down through the two-phase flow conduit 326 and enter the phase separator 334. In the phase separator 334, the gas that has been cooled but not liquified is separated from the liquid condensate and is removed from the phase separator 334 through the non-condensible gas conduit 338. As described above, the non-condensible gas conduit 338 is passed alongside the transfer line 344 at a second pre-cooling heat exchanger 330, and the waste gas is also passed around a coil 340 formed by a continuation of the feed line 212 in an annulus 342 comprising the first pre-cooling heat exchanger 328. The non-condensible waste gas from the phase separator 334 is joined by boil-off from the condensate in the storage dewar 324 in the annulus 342 to further cool the incoming feed gas. The waste gases and the boil-off are then released to the atmosphere through the discharge conduit 332. The liquified feed gas exits the phase separator 334 and is carried down the liquid conduit 336 for collection in the storage dewar 324.

In general, the insulating member 322 improves the efficiency and the performance of the cryogenic subsystem 300 by insulating the cold portions of that subsystem from ambient temperatures. The insulating member 322 may be evacuated to reduce the heat flow from the components at the ambient temperature to the low temperature parts. In that case, adsorbent 350 and getter 352 may be enclosed in the vacuum space. After establishing the desired vacuum level through evacuation tube 354, the evacuation tube 354 is sealed by pinching and soldering.

Figure 4:
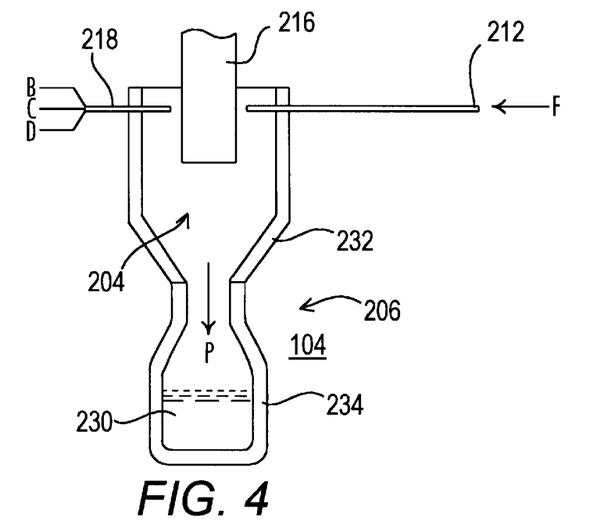
FIG. 4 is a schematic depiction of the flow of gases and liquids through the cryogenic subsystem of the present invention.

Referring now to FIG. 4, the material balance of the cryogenic subsystem 104 according to the present invention will be explained in the context of an oxygen-enriched feed gas supplied from an oxygen concentrator. As shown in FIG. 4, the feed gas F is introduced, via the feed tube 212, to the cryogenic subsystem 104, illustrated schematically in FIG. 4, and liquified oxygen, indicated as stream P in FIG. 4, is produced in the heat exchanger assembly/condenser 204.

The liquid oxygen is stored as a condensate 230 in the dewar 234. For a net liquid oxygen production of 40 grams per hour (stream P), approximately 60 grams per hour of feed gas F must be provided. A 60-gram per hour feed stream is a rate typically available from known medical oxygen concentrators 102. Streams B, C and D represent waste gases leaving the cryogenic subsystem 104 through waste conduit 218. The largest component of the waste stream is the boil-off stream B. In the given example, the boil-off stream B consists of approximately 12 grams per hour of oxygen. The boil-off stream B is a result of heat leak from the ambient atmosphere through the storage dewar 234. Of the waste streams, stream B is the largest consumer of the cryogenic subsystem's 104 refrigeration capacity. This is because it has the largest mass flow, and because it has been liquified, and thus has had a quantity of latent heat removed.

Waste stream C consists of non-condensed gases flowing at a rate of approximately 7 grams per hour. This stream is relatively rich in argon and also contains nitrogen and oxygen. Waste stream D represents an overfeed from the feed line 212 to the cryogenic subsystem 104, and thus is gas that the cryogenic subsystem does not have the cooling capacity to liquify. The overfeed is desirable to assure a small positive pressure in the storage dewar 234 to prevent the leakage of warm ambient air into the cryogenic subsystem 104.

The energy expended in cooling the waste streams B, C and D can be partly recovered through the use of precooling heat exchangers. Thus, in the precooling heat exchangers, the feed gas F is cooled by the waste streams B, C and D before it is condensed in the sensible heat exchanger. The latent heat expended in liquefying the boil-off stream B cannot be recovered, but the amount of boil-off can be minimized through the use of a well-insulated dewar 234. Approximately 40% of the refrigeration capacity used by the waste streams is lost in the phase change of the boil-off stream B.

In a preferred embodiment, the cryocooler 202 operates on the Stirling cycle. A typical linear Stirling type cryocooler suitable for use in connection with the disclosed method and apparatus provides a rated 4 watts of refrigeration at 77K. The actual refrigeration capacity of the disclosed embodiments of the present invention is about twice the rated capacity, because the boiling points of the gases supplied by the oxygen concentrator 102 are somewhat higher than 77K, and because precooling is used.

Figure 5:
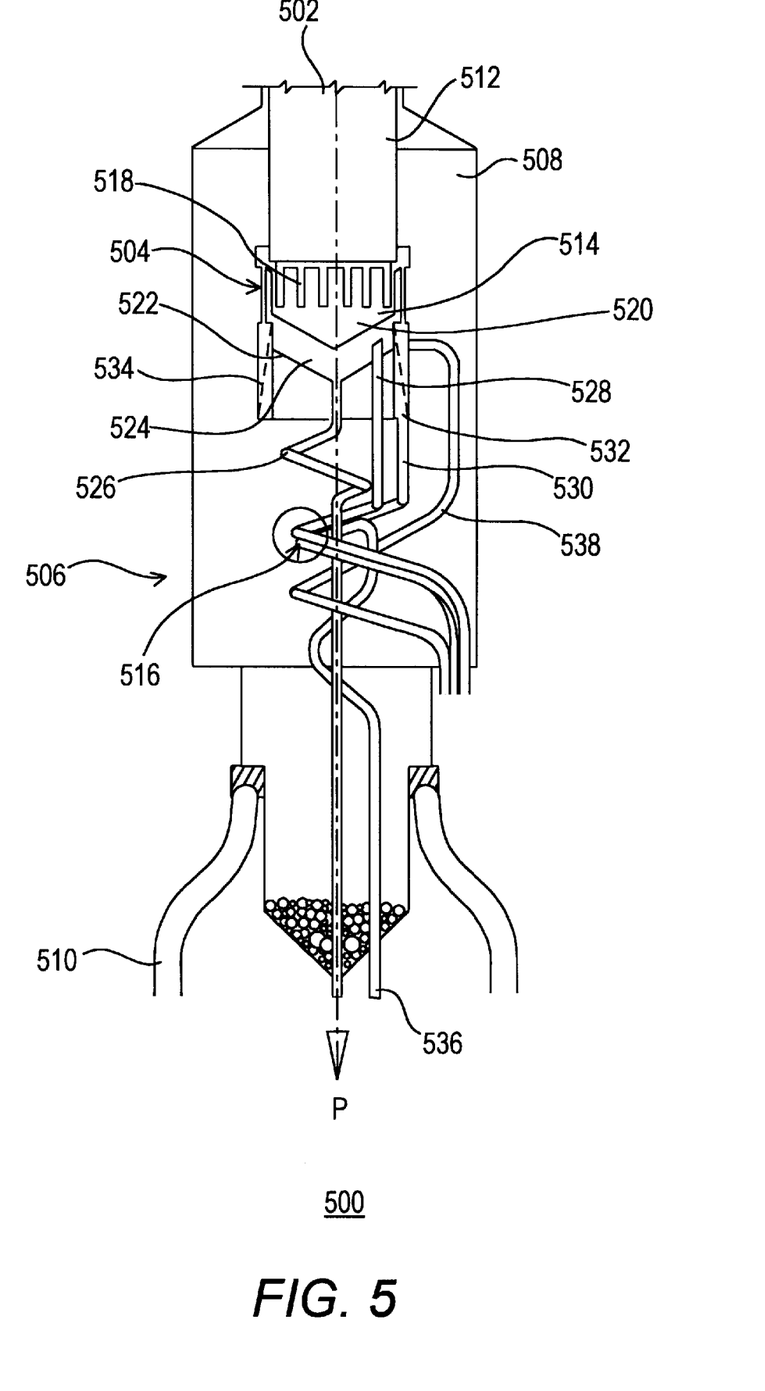
FIG. 5 is a partial depiction of the major components of an embodiment of the cryogenic subsystem of the present invention.

Referring now to FIG. 5, an alternative embodiment 500 of the cryogenic subsystem 104 of the apparatus for producing and storing liquid gas is partially illustrated in cross section. The cryogenic subsystem 500 of the present embodiment generally includes a cryocooler 502, a heat exchanger assembly 504, and an insulated subsystem 506. The components comprising these subsystems are generally similar to those described above with reference to the first described embodiment, however, the configuration of the components differs.

The insulated subsystem 506 generally comprises an insulated member 508 and a storage dewar 510. The cold finger 512 only of the cryocooler 502 is visible in FIG. 5, and is surrounded by the insulated member 508 to improve the efficiency of the device.

The heat exchanger assembly 504 includes a sensible heat exchanger/condenser 514 and a precooling heat exchanger 516. The sensible heat exchanger/condenser 514 includes cooling fins 518 in contact with the cold finger 512 of the cryocooler 502. Surrounding the cooling fins 518 of the sensible heat exchanger/condenser 514 is the condenser volume 520. Condensate formed in the sensible heat exchanger/condenser 514 falls and is collected in the condensate collector 522. The condensate collector 522 is part of a phase separator 524. From the phase separator 524, condensate exits via liquid conduit 526. Waste gas then exits the phase separator 524 via the waste gas conduit 528.

Feed gas is supplied to the sensible heat exchanger/condenser 514 through the feed line 530. The outlet of the feed line 530 is in communication with an annular space 532, which contains a screen 534. The screen 534 is preferably made of high conductivity copper, and is thermally joined to the cold, upper portion of the phase separator 524 at a first end, and to the lower portion of the annular space 532 at a second end.

Boil-off from the liquid condensate in the dewar 510 exits the dewar 510 through the boil-off return conduit 536. A portion of the boil-off return conduit 536, the waste gas conduit 528, and the feed gas tube 530 form a precooling heat exchanger 516 by being arranged so that the boil-off 536 and waste gas 528 conduits are in thermal contact with the feed gas tube 530. Thus, heat from the feed gas in the feed gas tube 530 is transferred to the gases in the waste gas 528 and boil-off conduits 536.

According to the embodiment illustrated in FIG. 5, feed gas entering the cryogenic subsystem 500 must pass through the screen 534 before entering the sensible heat exchanger/condenser 514. Because the screen 534 is in thermal contact with the cold, upper portion of the phase separator 524, most condensible impurities contained in the feed gas will be deposited on the cold screen 534. This configuration helps prevent clogging of the feed line 530 and the sensible heat exchanger/condenser 514 with rime. The screen 534, however, can eventually itself become clogged with rime. Therefore, provisions have been included to purge rime from the system when desired.

In order to remove rime, a purge conduit 538 is provided to admit dry, relatively warm air to the annular space 532. The introduction of warm, dry air to this area has the effect of thawing and back purging any impurities deposited on the screen 534 and the outlet of the feed tube 530. Generally, it is beneficial to purge the system of rime approximately every 30–60 days.

Figure 6:
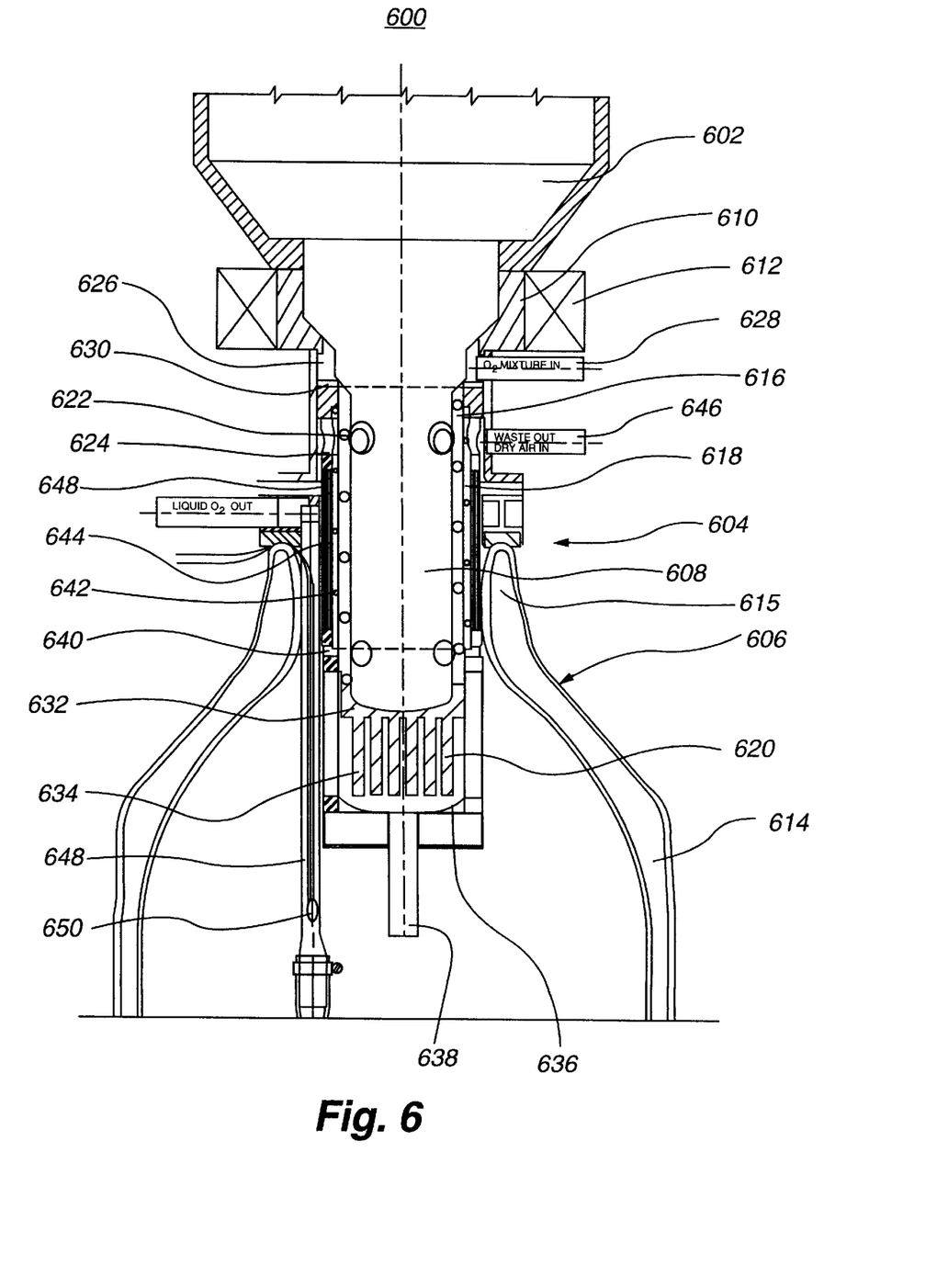
FIG. 6 is a partial depiction of the major components of an embodiment of the cryogenic subsystem of the present invention.

Referring now to FIG. 6, a third, preferred embodiment of the present invention is illustrated. The cryogenic subsystem 600 partially illustrated in FIG. 6 generally includes a cryocooler 602, a heat exchanger assembly 604, and an insulated subsystem 606. As with the other illustrated embodiments, the cryogenic subsystem 600 is preferably arranged so that the cryocooler 602 is disposed vertically above the insulated subsystem 606, with at least portions of the heat exchanger assembly 604 disposed within a volume described by the insulated subsystem 606.

The cryocooler 602 generally includes a cold finger 608, which is the coldest part of the cryocooler 602. In addition, the cryocooler 602 includes a heat rejection area 610, which, as with the earlier described embodiments, may feature cooling fins 612 to assist in dissipating waste heat from the cryocooler, thus increasing the efficiency of the device 600. Alternatively, or in addition, the heat rejection area 610 may be cooled by a vapor-compression refrigeration system or other cooling system (not shown).

The insulated subsystem 606 of the illustrated embodiment generally includes a storage dewar 614. As can be seen from FIG. 6, the neck portion 615 of the storage dewar 614 receives a substantial portion of the heat exchanger assembly 604. Accordingly, the dewar 614 of the insulated subsystem 606 provides insulation for the cold components of the heat exchanger assembly 604 from the ambient atmosphere.

The heat exchanger assembly 604 generally includes an inner heat exchanger 616, an outer heat exchanger 618, and a sensible heat exchanger/condenser 620.

The inner heat exchanger 616 in the illustrated embodiment is comprised of the outer surface of the cold finger 608, the inner helix 622, and an inner sheath 624. When the system is in operation, feed gas enters an annular space 626 after exiting the feed gas tube 628. The feed gas passes through slots in the support ring 630 to enter the inner heat exchanger 616. Feed gas introduced to the inner heat exchanger 616 is gradually cooled as it travels along the helical path defined by the inner helix 622, the cold finger 608, and the inner sheath 624. After traveling the entire length of the inner heat exchanger 616, the feed gas is introduced to the sensible heat exchanger/condenser 620.

The sensible heat exchanger/condenser 620 includes a knurled section 632, which is itself part of the sensible heat exchanger/condenser 620. The feed gas, which has been progressively cooled by the inner heat exchanger 616, is condensed on the cooling fins 634 of the sensible heat exchanger/condenser 620. The condensate thus formed is collected in the condensate collector 636 and removed from the sensible heat exchanger/condenser 620 to the storage dewar 614 by passing through the liquid conduit 638.

The embodiment illustrated in FIG. 6 also includes an outer heat exchanger 618 to recycle refrigeration capacity expended in cooling waste gases and in liquefying desired components of the feed gas (e.g., oxygen) that is condensed but later boiled off from the condensate due to heat leak through the storage dewar 614. The non-condensible waste gases and the boil-off from the oxygen condensate are removed from the interior volume of the storage dewar 614 through return stream ports 640. The waste gases then travel through the outer heat exchanger 618, cooling the feed gas as described further below.

The outer heat exchanger 618 is generally formed from the inner sheath 624, the outer helix 642, and the outer sheath 644. As the waste gases follow the helical path defined by the inner sheath 624, the outer helix 642, and the outer sheath 644, the inner sheath 624 is cooled. As the feed gas is in contact with the surface of the inner sheath 624 opposite the surface defining a portion of the outer heat exchanger, the feed gas is cooled by the waste gases. The waste gas exits the outer heat exchanger through the waste conduit 646. Upon exiting the outer heat exchanger 618, the waste stream is at or near the ambient temperature.

The inner sheath 624 of present embodiment is preferably constructed from a thermally conductive material. This assists in cooling the feed stream by facilitating the transfer of heat from the feed stream traveling down the inner heat exchanger 616 to the waste stream traveling up the outer heat exchanger 618. In a preferred embodiment, the inlet sheath 624 is constructed from stainless steel of approximately 0.003 inches in thickness. The outer sheath 644 may be constructed of a nonconductive material, such as plastic. In a preferred embodiment, the outer sheath 644 is constructed from a thermally nonconductive material. According to one embodiment, the outer sheath 644 is 0.005 inch thick Mylar. In a preferred embodiment, an insulation layer 648 is provided about an exterior of the outer heat exchanger 618 to prevent the loss of cooling capacity from the outer heat exchanger 618 to the ambient air.

The embodiment illustrated in FIG. 6 is thermodynamically more efficient than the earlier described embodiments. This is because the transfer of heat from the incoming feed gas occurs across smaller temperature differences. In addition, the ratio of the length of the dewar 614 to the diameter of the neck 615 of the dewar is less than 2:1, and preferably is about 1:1 or less. This allows the sensible heat exchanger/condenser 620 to be placed substantially inside of the dewar 614, reducing the temperature differential and therefore reducing losses from the coldest parts of the inner heat exchanger 616 and the sensible heat exchanger/ condenser 620. This arrangement also reduces the need for vacuum insulation separate from the dewar 614 around the heat exchanger assembly/condenser 604. Also, the embodiment illustrated in FIG. 6 is advantageous because the large cross sectional area of the flow paths provided for the incoming feed air in this embodiment are sufficient to prevent the deposition of rime from blocking that flow. Accordingly, the system can be run for long periods of time between purgings to remove deposits. The embodiment of FIG. 6 also provides a liquid conduit 638 having a short length and a large diameter, further increasing efficiency.

The purging of the system to remove deposits may be accomplished through the introduction of dry, warm air or, conveniently, flow from the concentrator through the waste conduit 646 or inlet conduit 628. The occasional purging of the device in this way removes deposits from the surfaces of the heat exchanger assembly 604 from the sensible heat exchanger/condenser 620 and from the storage dewar 614.

To remove collected condensate from the storage dewar 614, the vapor space above the liquid condensate in the dewar 614 is pressurized to a level not exceeding 10 pounds per square inch greater than atmospheric pressure. This pressurization of the volume enclosed by the dewar 614 expels the liquid condensate through the lower fill tube 648 for transfer to, for example, a portable dewar. The lower fill tube 648 may also be used to mount the liquid level sensor ball 650. When the level of condensate reaches the level of the ball 650, the system may be turned off, to prevent the overflowing of the storage dewar 614.

As described above, the inner sheath 624 is preferably constructed from a thermally conductive material, such as stainless steel. The inner 622 and outer 642 helixes may be constructed from Teflon tubing, to facilitate the assembly of the inner 616 and outer 618 heat exchangers. The cooling fins 634 of the sensible heat exchanger/condenser 620 are preferably constructed from a material having a good thermal conductivity.

The design of the sensible heat exchanger/condenser 620 will now be explained. The required surface area of the cooling fins 634 for a given rate and temperature of incoming feed gas is a function of the cryocooler 602 performance and cold finger 608 temperature. Many configurations are possible in accordance with the present invention. For example, it is known that providing a surface such as a Gregorig surface or other finned surface where the grooves and the fins run vertically, provide heat transfer results that are superior to a smooth surface, thus reducing the required surface area. These surfaces, through the action of the surface tension of the condensate, ensure a thin film in the direction of liquid flow on part of the surface, while providing a large hydraulic diameter at other portions, ensuring fast drainage of the film. The usage of such surfaces, however, is of questionable value, since the cost of the required condenser surface area as compared to the cost of the rest of the assemblies is exceedingly small. Furthermore, should fouling of the surfaces occur, the finned design, with an excess surface area, will give the best long term performance.

Where the cryocooler has adequate cooling capacity, condensation can be carried out on the cold finger itself, without employing a separate condenser. Ridges impressed onto the cold finger in the direction of the gravity flow of the condensate will provide fast draining in the valleys between ridges, while thinning the condensate film on the crests of the ridges, thus increasing the condensation rate.

Somewhat similarly, the need for insulation is also dependent on the performance of the cryocooler 602. Since the temperature difference inside of the storage dewar 614 between the cold parts of the sensible heat exchanger/condenser 620 and the dewar 614 atmosphere is very small, a small percent of excess capacity will reduce the need for good insulation, allowing even plastic film or solid insulation to be used. Alternatively, if all of the cooling capacity of the cryocooler 602 must be used, an aerogel insulation, which will assure very low heat flow even without a vacuum, can be used.

The storage dewar 614 may be any well-insulated storage container. For example, the storage dewar 614 may be a standard 1.8 liter glass vacuum insulated dewar.

Figure 7:
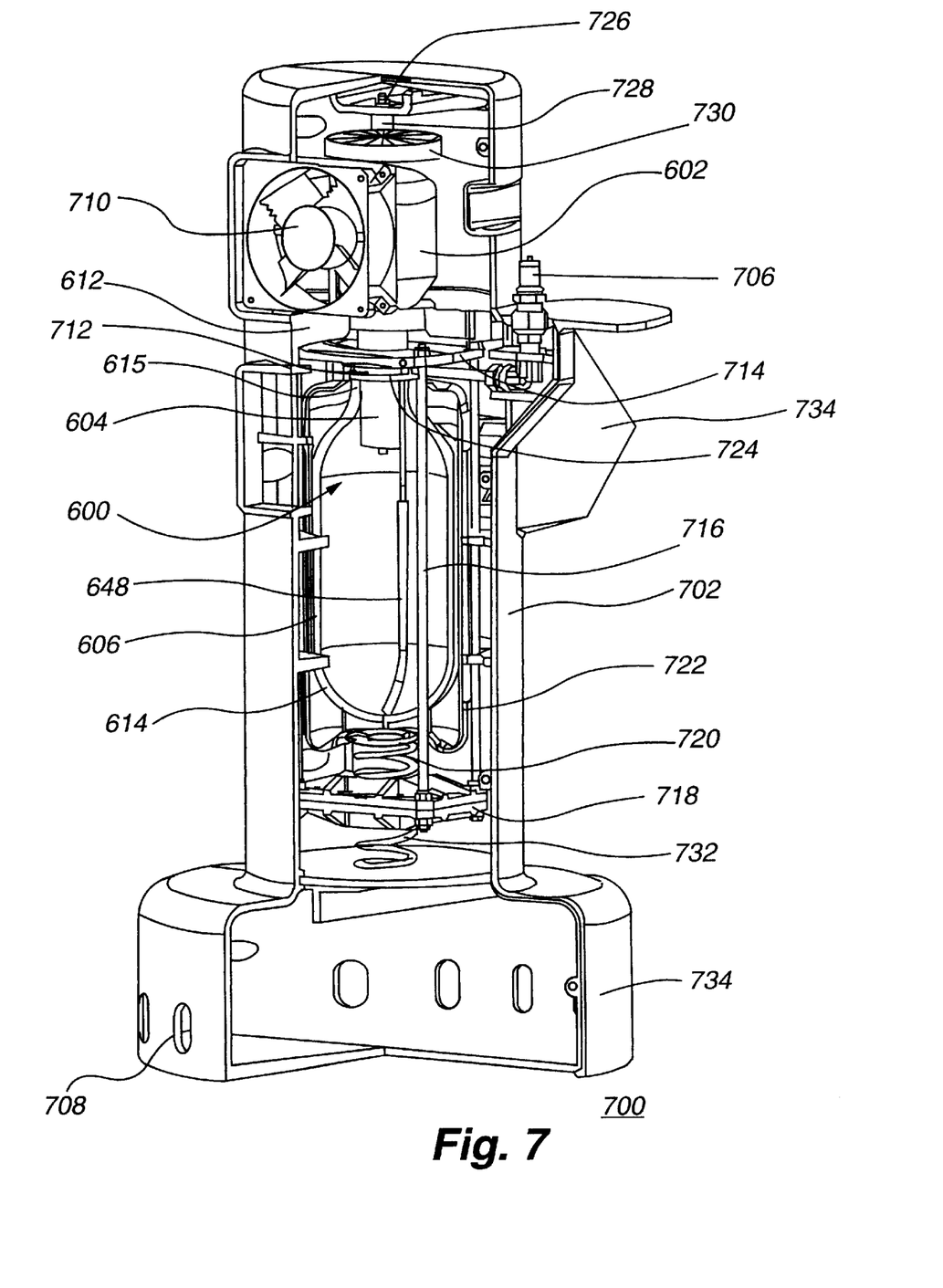
FIG. 7 is a partially cutaway perspective view of a cryogenic subsystem according to an embodiment of the present invention.

Referring now to FIG. 7, a liquefier assembly 700 is depicted. According to the embodiment shown in FIG. 7, the cryogenic subsystem 600 is enclosed in a casing 702. Visible in FIG. 7 are the major components of the cryogenic subsystem 600, including the cryocooler 602, the heat exchanger assembly 604 and the insulated subsystem 606. The storage dewar 614 of the insulated subsystem can be seen in FIG. 7 in its preferred position, below the cryocooler 602, and below and surrounding the heat exchanger assembly 604. This configuration allows condensate formed in the heat exchanger assembly 604 to fall into the storage dewar 614 by gravity. In the embodiment illustrated in FIG. 7, the storage dewar 614 of the insulated subsystem 606 extends upwardly so that it surrounds a substantial portion of the heat exchanger assembly 604, insulating the cold components of the heat exchanger assembly 604 from the ambient air.

Also seen in FIG. 7 is the lower fill tube 648. The lower fill tube 648 can be seen to extend down to the bottom of the storage dewar 614 and to exit the storage dewar at the neck of the dewar 615. The lower fill tube 648 turns at the neck or opening 615 the storage dewar 614 to interconnect to the liquid transfer fitting 706. The liquid transfer fitting 706 may be used to transfer liquified gas produced by the liquefier assembly 700 into portable storage dewars (not shown). In this way, liquified gas produced by the liquefier assembly 700 may be used in locations distant from the unit.

The casing 702 is provided with apertures 708 for allowing the entry of ambient air into the casing 702. This ambient air is drawn through the casing 702 around the cooling fins 612 of the cryocooler 602 and drawn out of the casing 702 by the fan 710.

FIG. 7 also illustrates the interconnection between the cryocooler 602, together with the attached heat exchanger assembly 604, to the insulated subsystem 606. In particular, the cryocooler 602 is provided with a flange 712, which carries flange plate 714. Flange plate 714 is interconnected through tie rods 716 to the spring plate 718. The spring plate 718 in turn supports the insulated subsystem 606 through upper spring 720, which bears against the protective shell 722 of the storage dewar 614. In this way, the seal 724 between the neck 615 of the storage dewar 714 and the flange 712 can be broken if the pressure inside the storage dewar 614 exceeds a predetermined limit. For example, the upper spring 720 may be selected so that the seal 724 is broken if the pressure inside the storage dewar 614 exceeds the pressure used to transfer liquid condensate out through the lower fill tube 648 to a portable storage dewar by a predetermined amount. Thus, according to a presently preferred embodiment, the seal 724 may be broken when the pressure inside the storage dewar 614 exceeds 10 pounds per square inch.

However, it should be noted that the cryogenic subsystem 600 has a liquid level that is self limiting. This is because, as the level of the condensate in the storage dewar 614 rises, the length of the heat paths from the interior of the dewar 614 to the ambient atmosphere decreases. Therefore, it will be understood that the liquid level sensor ball 650, used to trigger a signal to stop production of liquefied gas, and the upper spring 720 calibrated to break the seal 724 in response to an over-pressure in the storage dewar 614, are simply additional safety measures, and are not necessary to the functioning of the cryogenic subsystem 600.

The cryocooler 602 and the attached heat exchanger assembly/condenser 604 are affixed to the casing 702 through a bolt 726 and an associated grommet 728. Below the grommet 728 is the balancing assembly 730 of the cryocooler 602 which reduces the axial vibration of the Stirling unit. At a bottom end, the spring plate 718 may be supported in part by lower spring 732. The use of the elastomeric grommet 728 in combination with the lower spring 732 serves to insulate the casing 702, and thus the ambient environment, from vibration produced within the cryocooler assembly 602. Also illustrated in FIG. 7 is instrument panel 734, which contains the controls and the displays associated with the operation of the assembly 700. A compressor and adsorber (not illustrated in FIG. 7) may be mounted in the lower portion 734 of the casing 702. The operation of these components will be described below.

Figure 8:
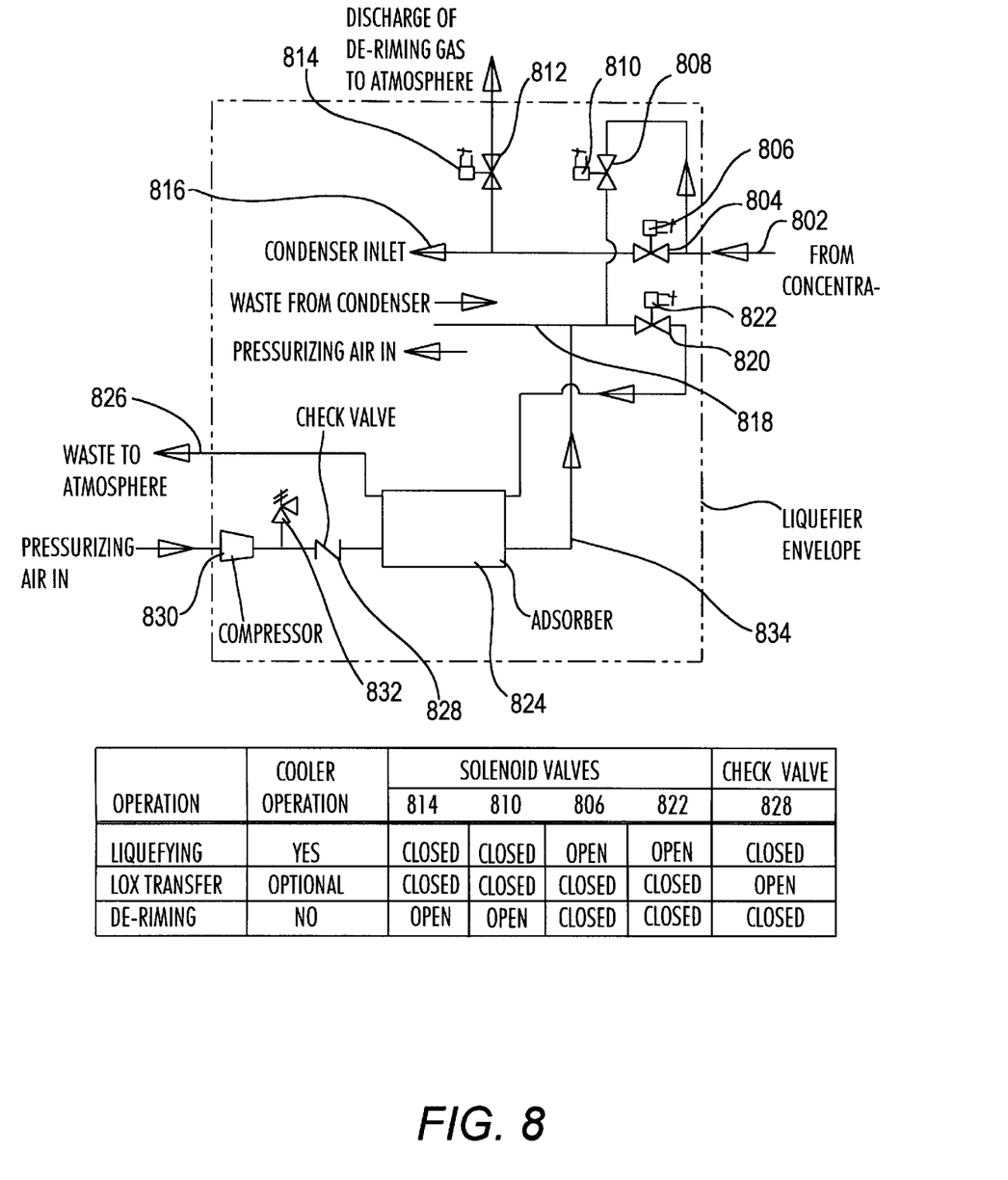
FIG. 8 is a schematic depiction of the control valves and flow paths associated with use of the disclosed system.

Referring now to FIG. 8, a schematic representation of the control valves used to perform various operations involving the cryogenic subsystem 104 are illustrated. During normal liquefying operation, the gas to be liquified is introduced to the cryogenic subsystem through a feed gas tube 802. The feed inlet valve 804, shown with an associated solenoid control unit 806, is open, and the de-riming inlet valve 808, shown with associated solenoid 810, is closed. The de-riming outlet valve 812, shown with associated solenoid 814, is also closed. Accordingly, during liquefying, the feed gas enters the system through the feed gas tube 802 and travels directly to the condenser inlet 816, where it is liquified. During liquification, waste gas from the condenser enters the waste gas inlet 818 and passes through the open waste gas valve 820, shown with associated solenoid 822. The waste gas also is passed through the adsorber 824, to cleanse the adsorber 824 and regenerate its adsorption properties. Preferably, the length of the conduit between the waste gas inlet 818 and the adsorber 824 is long enough to reduce the temperature of the waste gas to about room temperature before it is introduced to the adsorber 824. The waste gas is then vented to the atmosphere through waste gas outlet 826.

When the transfer of gas condensate from the storage dewar to a portable storage dewar is desired, the operation of the cryocooler is optionally stopped. The feed gas inlet valve 804, the de-riming inlet valve 808, the de-riming outlet valve 812, and the waste gas valve 820 are all closed. Check valve 828 is opened, and the compressor 830 is operated to force ambient air into the adsorber 824. The connection between the compressor 830 and the adsorber 824 may be provided with a pressure relief valve 832 to keep the pressure around 10 psig. The adsorber 824 contains a desiccant to remove moisture from the incoming compressed air, and helps to prevent the introduction of impurities into the interior of the system. The pressurized air leaves the adsorber 824 through the pressurized air conduit 834, which interconnects to the waste outlet 818, through which the pressurized air enters the interior of the storage dewar. The pressure thus introduced to the interior of the storage dewar forces the liquified gas out through the lower fill tube (not illustrated in FIG. 8) as described above. In a preferred embodiment, a transfer pressure of between 8 and 10 pounds per square inch is used to force the condensate from the dewar.

It is also desirable to provide for the de-riming of the cryogenic subsystem 104. De-riming is desirable because, over time, water vapor introduced by the feed gas may foul the components of the heat exchanger assembly/condenser and the feed gas conduit. Also, moisture and contaminants are introduced to the interior of the cryogenic subsystem 104 during the transfer process. To de-rime the system, the operation of the cryocooler is halted. The de-riming inlet valve 808 and the de-riming outlet valve 812 will both be open. The feed gas inlet valve 804 and the waste gas valve 820 will be closed. With the valves thus configured, feed gas is introduced to the interior of the storage dewar through the waste gas outlet 818. The gas, thus fed, then may pass over the interior components of the heat exchanger assembly/condenser, which in the off state is warmed by the feed gas, allowing contaminants to evaporate. The contaminants are expelled from the system through the de-riming outlet valve 812 to the ambient atmosphere.

Alternatively, the de-riming flow may be introduced to the system through the condenser inlet 816 and vented to the atmosphere from the waste gas outlet 818.

Although the embodiments discussed in detail above were generally described with reference to use in combination with an oxygen concentrator, this need not be the case. For example, the cryogenic subsystem 104 of the present invention may be used with concentrators adapted to provide enriched feed gases comprising other components of air, such as nitrogen. Also, the cryogenic subsystem 104 may be used in combination with gases that have been purified at another site, for liquification by the cryogenic subsystem 102 at the point of use. Additionally, the described cryogenic subsystem 102 may be used to liquefy ambient air.

Other alterations and modifications are also contemplated by the inventors. For example, the transfer of liquified gas to a portable insulated container may be performed using dry air or another gas such as nitrogen from a pressurized cylinder in combination with a pressure regulator. Alternatively, the transfer may be accomplished by warming the condensate, or by use of a pump.

In accordance with the present invention, an apparatus for producing and storing liquid oxygen in an oxygen patient's residence is provided. The invention in its broader aspects relates to a system that forms an oxygen enriched gas from ambient air, for use by an oxygen patient. More particularly, the invention provides a method and apparatus for liquefying oxygen produced in the residence of an oxygen patient for storage and later use. In addition to its usefulness in liquefying oxygen, the disclosed cryogenic subsystem of the present invention may used in the liquification of other gases.

The foregoing description of the present invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode known for practicing the invention and to enable others skilled in the art to utilize the invention in such, or in other, embodiments and with various modifications required by the particular application or use of the present invention. It is intended that the appended claims be construed to include alternative embodiments to the extent permitted by the prior art.

What is claimed is:

1. An apparatus for producing and storing liquid gas comprising:
   a device for supplying a feed gas;
   a cryocooler, wherein said cryocooler includes a cold finger;
   a heat exchanger assembly cooled by said cryocooler, wherein said heat exchanger assembly comprises:
      an inner helix disposed about a periphery of said cold finger;
      an inner sheath disposed about said inner helix to form a feed gas conduit;
      a cooling fin thermally interconnected to said cold finger; and
   a dewar, surrounding at least a portion of said heat exchanger assembly, wherein at least a portion of said feed gas introduced to said heat exchanger assembly is liquified in a portion of said heat exchanger assembly, and wherein a liquid condensate is collected in said dewar.

2. The apparatus of claim 1, wherein said heat exchanger assembly further comprises an outer heat exchanger comprising:
   an outer helix disposed about said inner sheath;
   an outer sheath disposed about said outer helix to form a waste conduit for a cold waste gas, wherein said cold waste gas passing through said waste conduit cools said inner sheath, which in turn cools said feed gas passing through said feed gas conduit.

3. The apparatus of claim 2, further comprising an insulation member disposed about said outer heat exchanger.

4. The apparatus of claim 1, further comprising a vapor-compression refrigerator for cooling a heat rejection area of said cryocooler.

5. The apparatus of claim 1, further comprising a source of pressurized gas for pressurizing an interior of said dewar, and a lower fill tube for removing at least a portion of said condensate from said dewar.

6. The apparatus of claim 5, wherein said source of pressurized gas comprises a compressor.

7. The apparatus of claim 5, further comprising an adsorber for removing moisture from said pressurized gas.

8. The apparatus of claim 1, wherein said dewar has a length and an opening diameter, and wherein a ratio of said length to said opening diameter is less than about 2:1 .

9. The apparatus of claim 1, wherein said heat exchanger assembly is located substantially inside of said dewar.

10. The apparatus of claim 1, wherein the feed gas is gradually cooled from a temperature at which the feed gas is in a gaseous state at an ambient pressure to a temperature at which the feed gas is in a liquid state at a pressure less than about 10 psig.

11. The apparatus of claim 1, wherein said heat exchanger assembly has a length that is about equal to the length of said cold finger of said cryocooler, plus a length of said cooling fin at an end of said cold finger distal from said cryocooler.

12. The apparatus of claim 1, further comprising:

a casing; and an upper spring, wherein said dewar is pressed against a flange to form a seal, and wherein said upper spring is calibrated to release said seal when a pressure inside said dewar exceeds a predetermined amount.

13. The apparatus of claim 12, wherein said predetermined amount is greater than about 10 psig.

14. The apparatus of claim 1, wherein said dewar is constructed of glass.

15. The apparatus of claim 1, wherein said device for supplying a feed gas supplies an oxygen enriched feed gas from ambient air.

16. An apparatus for liquefying and storing an enriched gas, comprising:

a feed gas source;

a cryocooler having a cold finger;

a heat exchanger assembly, at least of a portion of which is thermally interconnected to said cold finger;

an insulated subsystem wherein said insulated subsystem comprises:
an insulating element having open first and second ends wherein said first end of said insulated element surrounds at least a portion of a periphery of said heat exchanger assembly and a length of said insulating element extends beyond an end of said heat exchanger assembly;
a dewar having an open end in communication with said second end of said insulating element; and a feed gas tube having an inlet for receiving said feed gas from said feed gas source and an outlet, wherein feed gas is delivered from said outlet to said heat exchanger assembly, and wherein said feed gas is cooled by said heat exchanger assembly to form a condensate.

17. The apparatus as claimed in claim 16, wherein said heat exchanger assembly further comprises a sensible heat exchanger, and wherein said sensible heat exchanger includes cooling fins and a condensate collector.

18. The apparatus as claimed in claim 17, wherein said cooling fins are integral to said cold finger.

19. The apparatus as claimed in claim 16, wherein said heat exchanger assembly comprises a first pre-cooling heat exchanger.

20. The apparatus as claimed in claim 19, wherein said heat exchanger assembly further comprises a second pre-cooling heat exchanger.

21. The apparatus as claimed in claim 19, wherein said first pre-cooling heat exchanger comprises:

a coil formed from a portion of said feed gas tube in an annular space, wherein waste gas is passed through said annular space.

22. The apparatus as claimed in claim 16, further comprising a vapor-compression refrigerator for cooling a heat rejection area of said cryocooler.

23. The apparatus as claimed in claim 16, further comprising cooling fins thermally connected to a heat rejection area of said cryocooler.

24. The apparatus as claimed in claim 16, wherein said feed gas source is a device for producing an enriched gas from ambient air.

25. The apparatus as claimed in claim 16, wherein said feed gas is selected from the group consisting of oxygen, argon, nitrogen, fluorine, and air.

26. The apparatus as claimed in claim 16, further comprising:

a compressor operatively connected to an interior volume of at least a portion of said insulated subsystem; and a lower fill tube disposed within said interior volume of at least a portion of said insulated subsystem, wherein said compressor pressurizes said interior volume to force said condensate of said feed gas out said lower fill tube.

27. The apparatus as claimed in claim 16, wherein said dewar is constructed of glass.

28. A method for producing and storing a liquefied gas comprising:

providing a feed gas;

providing a cryocooler having a cold finger and a sensible heat exchanger in thermal contact with said cold finger;

providing an insulated volume proximate to and surrounding a periphery of said sensible heat exchanger;

cooling said feed gas to a temperature less than the condensation temperature of oxygen by delivering said feed gas to said insulated volume to produce a condensate;

removing said condensate from said insulated volume;

collecting said removed condensate in a dewar;

providing a source of pressurized gas located outside of said dewar;

pressurizing an interior of said dewar using said pressurized gas; and removing said condensate from said dewar through a fill tube.

29. The method of claim 28, further comprising:

de-riming said sensible heat exchanger by:
turning off said cryocooler;
delivering said feed gas to said dewar and to said insulated volume, wherein contaminants in said dewar and said insulated volume are evaporated; and
expelling said contaminants and said feed gas from said dewar and said insulated volume.

30. The method of claim 28, wherein said source of pressurized gas is a compressor.

31. The method of claim 28, wherein said pressurized gas contains moisture, and wherein said moisture is removed from said pressurized gas by an adsorber before using said pressurized gas to pressurize said interior of said dewar.

32. The method of claim 28, wherein said feed gas comprises oxygen.

33. The method of claim 28, wherein said step of cooling occurs over a length about equal to a length of said cold finger plus a length of said sensible heat exchanger.

34. The method of claim 28, wherein said dewar is constructed of glass.

* * * * *